US007361373B2

(12) United States Patent
Nam

(10) Patent No.: US 7,361,373 B2
(45) Date of Patent: Apr. 22, 2008

(54) ANTIPYROTIC AND METHOD OF MANUFACTURING THE SAME

(76) Inventor: Jong-hyun Nam, 26-5, Koyo-dong, Songpa-ku, 138-110 Seoul (KR)

( * ) Notice: Subject to any disclaimer, the term of this patent is extended or adjusted under 35 U.S.C. 154(b) by 306 days.

(21) Appl. No.: 10/483,167

(22) PCT Filed: Jan. 14, 2003

(86) PCT No.: PCT/KR03/00074

§ 371 (c)(1), (2), (4) Date: Feb. 28, 2005

(87) PCT Pub. No.: WO2004/009108

PCT Pub. Date: Jan. 29, 2004

(65) Prior Publication Data

US 2005/0158407 A1 Jul. 21, 2005

(30) Foreign Application Priority Data

Jul. 23, 2002 (KR) ..................... 10-2002-0043265

(51) Int. Cl.
*A61K 36/13* (2006.01)
*A61K 36/00* (2006.01)

(52) U.S. Cl. .................... 424/770; 424/725.1; 424/776

(58) Field of Classification Search ..................... None
See application file for complete search history.

(56) References Cited

U.S. PATENT DOCUMENTS 1,749,814 A * 3/1930 Hamilton ..................... 44/530
2,361,711 A * 10/1944 Starner ....................... 102/355
2,373,512 A * 4/1945 Starner ........................ 44/600
3,152,985 A * 10/1964 Stoertz et al. .............. 210/694
4,985,249 A * 1/1991 Sakagami et al. .......... 424/770
4,999,240 A * 3/1991 Brotz ......................... 442/376

FOREIGN PATENT DOCUMENTS

JP 08215294 * 8/1996
JP 09136375 * 5/1997
JP 2000044964 * 2/2000
JP 2002013067 * 1/2002

OTHER PUBLICATIONS

Haykiri-Acma, H. Energy Conversion and Management. 2003. vol. 44, pp. 155-162.*

* cited by examiner

*Primary Examiner*—Christopher R. Tate
(74) *Attorney, Agent, or Firm*—Galgano & Associates PLLC

(57) ABSTRACT

The present invention relates to an antipyrotic having compositions excellent for treating burn and a normally used carrier in a fixed ratio, and a method of manufacturing the same. The antipyrotic of the present invention has, as its main composition, a carbonized pine cone that is yielded by completely combusting selected pine cones put in a sealed container after washing and drying at a temperature of 100 to 300° C. and has, as an additive, a normally used carrier. As described in detail, the present invention provides provide a cream or ointment type of antipyrotic that can easily treat with excellent treating power serious burn more than the second degree burn as well as slight burn that does not require special treatment by medical specialist. Their treatment ability is excellent and they can shorten the treatment period considerably and leave almost no scars on the skin after complete healing. They are made of plant formulations and thus show almost no side effects to the human body. In the prior treatment of using gauze, the patients complain about pain caused as the gauze and the scab are exfoliated together, when the gauze is removed from the affected region after a certain period. However, the antipyrotic of the present invention can be applied to the affected region softly without causing pains and thus are convenient to use.

19 Claims, No Drawings

ANTIPYROTIC AND METHOD OF MANUFACTURING THE SAME

TECHNICAL FIELD

The present invention relates to an antipyrotic and a method of manufacturing the same. More particularly, it relates to a cream that is excellent for treating skin burn (also referred to as "burn") by adding, in a fixed ratio, compositions excellent for treating burn wounds to usual cream or ointment for skin application, and a method of manufacturing the same.

BACKGROUND ART

Ever since the first discovery of fire by mankind, fire has become one of those things which have important meaning in the history of civilization and is indispensable in man's life. But fire also has become one that gives damage to mankind due to careless usage and the damage was big. Burn is one of those damages from wrong usage. Bum can be as slight as burn by solar heat, and it can be so frightening as to lead to death when it is serious.

The causes of burn are mainly accidents at home and half of them can be prevented and carelessness is the main causes of them. Burn is classified into first degree, second degree, third degree, and fourth degree and this classification is important in taking a measure for treatment. The first degree burn is instantly generated when taking strong solar rays in the beach or when contacting exploding gases or hot liquids instantaneously and the affected region may be accompanied by pain and redness and may be healed without trace after a few days without special treatment. The second degree burn also is accompanied by redness and blisters are formed in the affected region, which appears to be somewhat swollen compared to the surrounding tissues. It is accompanied by serious pain and can leave scars after complete healing. The third degree burn is the case where all the layers of skin including epidermis and dermis are damaged, and the skin is dried and turned into white or black as if it is burned and loses the sense. Lastly, the fourth degree burn is a term that started to be used recently and is the case where hypodermic muscles, tendons, nerves, and skeleton tissues are damaged, along with all the skin layers.

As explained in detail above, the degree of burn is classified into first, second, third, and fourth, according to the area and depth of burn, and the causes of burn can include those by current, chemicals, heat, etc. Anyone can get burned slightly or seriously due to carelessness or unexpected accidents.

In the case of getting burned, the first treatment is the most important. If it is not treated properly or treated wrong in emergency, it can leave scars and the treatment period can be lengthened and other skin diseases can be accompanied.

By the way, when the burn is serious at home or in industry, the patient is moved to the hospital immediately, but when the patient or the patron determines it is not serious, he or she relies on self-treatment and often neglects the affected region. Meanwhile, the traditional treatments such as pouring "soju" of distilled liquor onto the affected region or applying soy sauce or sesame oil are known as an emergency treatment or measure for burn, but such treatments can never be an emergency treatment or measure and can only aggravate the affected region. In this case, an emergency treatment that can be executed at home easily and effectively is to let the affected region cool with tap water (cool water), and this has proven to be effective medically.

Meanwhile, general antipyrotic can include Vaseline gauze, ointment for skin disease for treating slight burn, M ointment of cream type containing beta-sitosterol of D chemicals, etc.

However, such conventional antipyrotic have the following problems. The gauze-typed antipyrotic isolates the affected region from outside air and this may delay recovery. Also, when the burn is suppurative, secretions and suppurative meterials can be attached to the gauze, and it can give pain to the patient when the gauze is substituted. Furthermore, the conventional antipyrotic are not excellent in their effects.

In other words, these conventional antipyrotic did not reach a satisfactory level in terms of treatment of burns, and in particular, it has a long way before an easy treatment for slight burn such as first and second degree burn is developed.

Therefore, to solve the problems mentioned above, the present inventor found a natural substance having remarkable results in treatment of burn, and completed this invention by applying the substance to the cream for treating burn.

DISCLOSURE OF THE INVENTION

Therefore, it is an object of the present invention to provide a cream or ointment type of antipyrotic that can easily treat, with excellent treating power, slight burn that does not require special treatment by medical specialists.

Another object of the present invention is to provide a cream or ointment type of antipyrotic that do not leave irreparable scars after treatment Still another object of the present invention is to provide low-priced antipyrotic, which can avoid ill practice of interrupting treatment due to expensive medical expanses of burn treatment and other burdens by making it possible to treat burn easily.

Yet another object of the present invention is to provide a method of easily manufacturing the antipyrotic mentioned above.

The present invention provides an antipyrotic including carbonized pine cones in a broad sense according to the present invention.

Other objects, features and advantages of the present invention and will become apparent upon reading the following detailed description of the preferred embodiments of the invention when taken in conjunction with the appended claims.

Meanwhile, the application range of the present invention will become clearer furthermore in the detailed description of the preferred embodiments below. However, it is to be appreciated that those skilled in the art can variously modify and change the embodiments without departing the scope and spirit of the present invention. Therefore, the detailed explanation below should be viewed as for only illustrating a preferred embodiment.

In order to achieve the above objects of the present, according to one aspect of the present invention, there is provided an antipyrotic having, as its main composition, a carbonized pine cone that is yielded by completely combusting selected pine cones put in a sealed container after washing and drying at a temperature of 100 to 300° C. and having, as an additive, a normally used carrier.

As mentioned above, the pine cone used as the main composition of the present invention is the seed of pine. Pine can be called Sol, Chamsol, Songmok, Solnamoo, Sohorinamu in Korea. Pine also is called red pine since the bark and the bud is red. It is also called female pine, Japanese red pine, Yodong red pine, unifoliate red pine in China. Pine is bifoliate, where two leaves form a couple. It is also called Isoosong, Ichimsong (denoting two-needle pine), Iripsong, etc., and all these names represent pine is bifoliate. Scientific term of pine is Pinus densiflora Siebold et Zuccarini. When pine seed pushes out new shoots, shoots with the testa come out above earth, and the number of shoots is about 4 to 9 and is 6 in most cases. Pine leaves deviating the shoots form a couple and come out with one confronting the other and the bottom portion is in the vagina that is about 2 or 3 mm in size. The vagina is dark brown and is alive as long as the leaves, without falling down. Meanwhile, there are female and male flowers in pine, which bloom in the last ten days of April and the first ten days of May. The male flower is elliptical and 4 to 9 mm in length. The end of the stamen spreads in the shape of the half moon and there are two anthers below filements. There are two wings in pollen. Meanwhile, the female flower is hung 2 or 3 at the end of the branch. The initial shape is circular or elliptical and is about 5 mm in length and is light violet in color. This is a collection of a multitude of female flowers, which is called a cone. This is what is called a pine cone in the present invention. Mature pine cones consist of various scaly leaves, and in a scaly leaf, two ovules are in contact, which later on become a seed with two wings. Young cones in spring before pollination are called storbile or conelet in English, instead of cones. Scaly leaves of the pine cone is in contact with the axis of the pine cone helically, its end is fat and big, its exposed part is near the diamond shape, and there is a protrusion in its center. When the pine cone is mature, the gap between scaly leaves become bigger and the seeds are fallen apart and come flying out.

Meanwhile, according to the present invention, the sesame oil may be added to the antipyrotic of the present invention whose main composition is the carbonized pine cone.

Preferably, the sesame oil may be added 1:1 to 2:1 in the weight ratio compared to the weight of the pine cone to the antipyrotic of the present invention.

Gold and silver powders may preferably be added, in a fixed ratio, to the antipyrotic of the present invention.

Oily material available commercially may preferably be added, in a fixed ratio, to the antipyrotic of the present invention.

Preferably, natural vitamin E (tocopherol) may be added, in a fixed ratio, to the antipyrotic of the present invention.

The bark extract of the Amur cork tree may preferably be added, in a fixed ratio, to the antipyrotic of the present invention.

Also, the bask extract of the Amur cork tree may preferably be yielded by washing and drying in the shade the bark, extracting for 1 to 8 hours at a temperature of 60 to 120° C., and enriching to 12 to 60 Brix at low temperature.

Preferably, white Vaseline (pharmacopoeia) and refined lanoline (pharmacopoeia) may be used in a fixed amount as a carrier.

The type of antipyrotic constituted as above according to the present invention can be formulated in any type known already, but preferably it is formulated for local application in the ointment or cream type, and most preferably it is in the cream type. Furthermore, the antipyrotic of the present invention can be applied in the field of human and animal. Since the formulation of the present invention is for medical purpose, the type and the composition should be acceptable pharmacologically.

The cream or ointment of the present invention for treating burn preferably contains the carbonized pine cone 5 to 30% by weight and more preferably 10 to 20% by weight. If the cream or ointment of the present invention for treating burn contains the carbonized pine cone less than 5% by weight, the effect for treatment is insignificant. If it exceeds 30% by weight, the excessive amount does not show increased effect.

Meanwhile, the carbonized pine cone is insoluble in water but can be dissolved by forming a salt with an acid.

As mentioned above, to form a soluble gel of the cream or ointment of the present invention containing the carbonized pine cone, organic acids are preferably used. It is especially preferable that they are selected from the group consisting of acetic acid, succinic acid, citric acid, tartaric acid, glutamic acid, and their mixture. The organic acid used in the present invention preferably uses 2.5 to 15% by weight and more preferably the weight ratio of organic acid: carbonized pine cone is 1:2.

Also, the cream or ointment of the present invention for treating burn is manufactured by mixing the carbonized pine cone used as the main composition properly with an organic acid, Vaseline, and a carrier, following the general method of forming cream or ointment. Here, the cream or ointment of the present invention is preferably weakly acid, that is, in the pH range of 4.5 to 5.5.

The cream or ointment-typed antipyrotic manufactured according to the constitutions of the present invention is excellent for treating burn through acceleration of epidermis formation, acceleration of tissue cell restoration, antibacterial activity, antifungal activity, strengthening of adhesive power, living body compatibility, stopping bleeding and healing wounds by decomposition by enzyme inside the skin to D-glucosamine, prevention of fibrin fiber generation, etc. The burn in treating burn above includes all kinds of burn such as general burn, burn by hot liquid and biochemical radioactive gases.

According to another aspect of the present invention, there is also provided a method of manufacturing an antipyrotic that is effective for burn includes the steps of:

(a) washing and drying selected pine cones;

(b) putting the dried pine cones in a sealed container and completely combusting them at a temperature of 100 to 300° C.;

(c) pulverizing the carbonized pine cones yielded at the combustion step b) by sieving them with 50 to 200 mesh; and (d) formulating a cream or an ointment by adding a carrier to the carbonized pine cones, which is the main composition of the antipyrotic, pulverized at the pulverization step and uniformly mixing the added carrier and the pulverized pine cones with a homogenizer.

Preferably, the combustion step b) may be executed in a non-sealed container.

Preferably, the sesame oil may be added, in a fixed ratio, to the antipyrotic.

It is preferred that gold and silver powders may be added, in a fixed ratio, to the antipyrotic.

It is also preferred that natural vitamin E (tocopherol) or oily material available commercially may be added, in a fixed ratio, to the antipyrotic.

Preferably, the bark extract of the Amur cork tree may be added, in a fixed ratio, to the antipyrotic.

Also preferably, the bask extract of the Amur cork tree may be yielded by washing and drying in the shade the bark, extracting for 1 to 8 hours at 60 to 120° C., and enriching to 12 to 60 Brix at low temperature.

The method of manufacturing the antipyrotic according to the present invention makes it easy to manufacture with simple processes creams or ointments that are excellent for treating various burns.

BEST MODE FOR CARRYING OUT THE INVENTION

The present invention will be described hereinafter in detail with reference to examples and experiments, but the present invention is not limited to them.

EXAMPLE 1

First, the pine cones with uniform size were selected from the natural species of pine cones. They were washed with purified water and dried in the shade. After confirming whether they were well dried, 1000 g of the dried pine cones were put in a sealed container if they are well dried and completely combusted for 2 hours at 200° C.

After complete combustion, they were left alone for 1 or 2 hours to let them cool, thereby yielding the carbonized pine cone. The latter pine cone was sieved, thereby yielding about 800 g of the carbonized pine cone powder that is the main composition for antipyrotic of the present invention.

EXAMPLE 2

Except that the combustion was executed in an open container, not in a sealed container, 800 g of the carbonized pine cone powder were yielded with the same procedures as Example 1

EXAMPLES 3 and 4

The antipyrotic of the present invention were manufactured by using the carbonized pine cones yielded respectively in Examples 1 and 2, by adding usual carriers to them such that they are each contained in 30% by weight, and by following usual cream formulation methods.

EXAMPLES 5 and 6

Except that 20% by weight of the sesame oil were added, the antipyrotic of the present invention were manufactured with the same procedures as Examples 3 and 4.

Here for the sesame oil, sesame that is solid and contains sesamolin as much as possible is used. The sesame that satisfies such conditions well was that produced at Goesan, ChoongBuk-province, Republic of Korea. The sesame was selected with a selector such that foreign substances were not contained and dried after washing. After complete drying, the sesame was parched at about 160° C. in a parcher immediately before water is completely evaporated and smoke is generated. This parched sesame is crushed with a crusher and oil is extracted for use by pressing with a compressor.

EXAMPLES 7 and 8

Except that 20% by weight of gold and silver powders were added, the antipyrotic of the present invention were manufactured with the same procedures as Examples 3 and 4.

EXAMPLES 9 and 10

Except that 20% by weight of oily material available commercially were added, the antipyrotic of the present invention were manufactured with the same procedures as Examples 3 and 4.

EXAMPLES 11 and 12

Except that 20% by weight of the bark extract of the Amur cork tree were added, the antipyrotic of the present invention were manufactured with the same procedures as Examples 3 and 4.

Here, the bark extract of the Amur cork tree was yielded by extracting at 100° C. for 5 hours and by enriching the solid portion to 15% at about 55° C.

Experiment 1

Experiment 1 is about a clinical experiment where the antipyrotic of the present invention is applied to the patients with the second degree burn.

1. Subject: a group of patients with the second degree burn
2. Object: antipyrotic containing the cream type of the carbonized pine cone powder manufactured according to each example of the present invention
3. Application: applying to the affected region three times a day with a fixed time interval
4. Period: one week from the time of getting burn Under the conditions mentioned above, the antipyrotic of the present invention were applied and the results are given in Table 1 below.

TABLE 1

| | Right after burn | After 2 days | After 4 days | After 1 week |
|---|---|---|---|---|
| Example 3 | X | Δ | □ | ○ |
| Example 4 | X | Δ | □ | ○ |
| Example 5 | X | Δ | □ | ○ |
| Example 6 | X | Δ | □ | ○ |
| Example 7 | X | Δ | □ | ○ |
| Example 8 | X | Δ | □ | ○ |
| Example 9 | X | Δ | □ | ○ |
| Example 10 | X | Δ | □ | ○ |
| Example 11 | X | Δ | □ | ○ |
| Example 12 | X | Δ | □ | ○ |
| Control (left alone without treatment | X | X | Δ | Δ |

X: serious pain and blisters in the affected region
Δ: heat in the affected region, slight pain
□: stinging feeling disappears, slight pain when the affected region is in contact
○: more than 95% of the affected region are healed completely, almost no scars are left, hyperpigmentation of skin color at the affected region is hard to notice.

Comparisons 1 and 2

Comparisons 1 and 2 are the case where a patient having the second degree burn as in Example 1 is treated with different antipyrotices.

Comparison 1 used M ointment for general home usage containing beta-sitosterol of cream type from D chemicals, and comparison 2 used Vaseline gauze for general hospital usage. The progresses of the treatment are shown.

Comparisons 1 and 2 were compared using the results of the treatment, without different clinical experiments The methods were chosen for the following reasons:

Firstly, due to the peculiarity of the clinical experiment for treating burn, it is difficult to separately select patients with the second degree burn.

Secondly, the selecting of animals as the subject of clinical experiment does not allow precise comparison with the subjects of the present invention.

Thirdly, the antipyrotic of comparisons 1 and 2 are used generally at home and in hospital. This makes it possible to compare the progresses of the treatments at several time lapses.

For the reasons mentioned above, Comparisons 1 and 2 are each itemized in Table 2 in the same way as Example 1.

TABLE 2

| | Right after burn | After 2 days | After 4 days | After 1 week |
|---|---|---|---|---|
| Comparison 1 | X | X | X | Δ |
| Comparison 2 | X | Δ | Δ | □ |

Particularly in Comparison 1, 60% of the affected region were healed nearly after 3 weeks, but scars were left and hyperpigmentation at the affected region was noticeable.

Experiment 2

To confirm the treating power of the antipyrotic of the present invention depending on the degree of burn, the patients with the first degree burn, the second degree burn, the third degree burn, and the fourth degree burn were treated one application a day and the rate of complete healing after 8 days was investigated. It is considered as being completely healed when proud flesh granulates and hyperpigmentation and scars disappear. The results are shown in Table 3.

TABLE 3

| | Number of | Number of completely healed patients at | | | | | | | Day 8 or |
|---|---|---|---|---|---|---|---|---|---|
| | patients | Day 1 | Day2 | Day3 | Day4 | Day5 | Day6 | Day7 | longer |
| First degree burn | 10 | — | — | — | — | 5 | 4 | 1 | — |
| Second degree burn | 8 | — | — | — | — | 4 | 2 | 1 | 1 |
| Third degree burn | 5 | — | — | — | — | — | 2 | 2 | 1 |
| Fourth degree burn | 2 | — | — | | | | — | 1 | 1 |

The first degree burn by sun light was completely healed with only one application.

From the comparison of Tables 1 and 2, the healing speed was much faster with the antipyrotic of the present invention than with the prior antipyrotic. When applied to the affected region, the antipyrotic of the present invention is in the cream type that is convenient to use, can minimize the pain of the patients, and showed an excellent effect that they do not leave scars after complete healing.

Also as shown in Table 3, the antipyrotic of the present invention shows the treating power even for serious burns such as more than the second degree burn and thus their treating ability is far more excellent than the prior antipyrotic.

Industrial Applicability

As described in detail above, the present invention provides provide a cream or ointment type of antipyrotic that can easily treat with excellent treating power serious burn more than the second degree burn as well as slight burn that does not require special treatment by medical specialist. Their treating ability is excellent and they can shorten the treatment period considerably and leave almost no scars on the skin after complete healing. They are made of plant formulations and thus show almost no side effects to the human body. In the prior treatment of using gauze, the patients complain about pain caused as the gauze and the scab are exfoliated together, when the gauze is removed from the affected region after a certain period. However, the antipyrofic of the present invention can be applied to the affected region softly without causing pains and thus are convenient to use. Also, the present invention provides the method of easily manufacturing the antipyrotic of the present invention.

What is claimed is:

1. A method of manufacturing an antipyrotic composition that is therapeutically effective for treating burns, comprising the steps of:

(a) washing and drying selected pine cones;

(b) putting the dried pine cones in a container and completely combusting them at a temperature of 100° to 300° C. to obtain carbonized pine cones;

(c) pulverizing the carbonized pine cones obtained during step b) by sieving them with a 50 to 200 mesh sieve; and (d) formulating said pulverized carbonized pine cones obtained in step (c) into a cream or an ointment by adding a pharmacologically-acceptable carrier to the pulverized carbonized pine cones, and uniformly mixing said carrier and said pulverized pine cones with a homogenizer.

2. The method according to claim 1, wherein the combustion step b) is executed in a sealed container.

3. An antipyrotic composition prepared according to the method of claim 1.

4. The antipyrotic composition according to claim 3, further comprising sesame oil which is added at a weight ratio of 1:1 to 2:1 compared to the weight of the carbonized pine cones.

5. The antipyrotic composition according to claim 3, further comprising gold and silver powders which are added, in a fixed ratio, to the antipyrotic composition.

6. The antipyrotic composition according to claim 3, further comprising commercially available oily material which is added, in a fixed ratio, to the antipyrotic composition.

7. The antipyrotic composition according to claim 3, further comprising bark extract of the Amur cork tree which is added, in a fixed ratio, to the antipyrotic composition.

8. The antipyrotic composition according to claim 7, wherein said bark extract of the Amur cork tree is obtained by washing and drying said bark in the shade, extracting for 1 to 8 hours at 60° to 120° C., and enriching to 12 to 60 Brix at low temperature.

9. The composition according to claim 3, wherein said composition is in the form of a cream.

10. The composition according to claim 3, wherein said composition is in the form of an ointment.

11. The composition according to claim 3, wherein said carrier is selected from the group consisting of petroleum jelly and lanolin.

12. The composition according to claim 3, wherein said carbonized pine cone comprises 5 to 30% by weight of said composition.

13. The composition according to claim 12, wherein said carbonized pine cone comprises 10 to 20% by weight of said composition.

14. The composition according to claim 3, wherein said carbonized pine cone is water-insoluble.

15. The composition according to claim 3, additionally comprising:

an organic acid selected from the group consisting of acetic acid, succinic acid, citric acid, lartaric acid, glutaric acid and a combination thereof.

16. The composition according to claim 15, wherein said composition is weakly acidic in the pH range of 4.5 to 5.5.

17. A method for treating burns comprising topically administering to a burn area a therapeutically effective amount of the antipyrotic composition according to claim 3.

18. The method according to claim 17, wherein said composition is in the form of a cream.

19. The method according to claim 17, wherein said composition is in the form of an ointment.

* * * * *